US010285863B2

(12) United States Patent
Watkins et al.

(10) Patent No.: US 10,285,863 B2
(45) Date of Patent: May 14, 2019

(54) PROTECTIVE HELMET HAVING A COVER PLATE KNOCK OUT ASSEMBLY

(71) Applicant: A.C.E. International Company, Inc., Taunton, MA (US)

(72) Inventors: James P. Watkins, East Taunton, MA (US); Edward L. Martin, Sharon, MA (US)

(73) Assignee: A.C.E. INTERNATIONAL COMPANY, INC., Taunton, MA (US)

( * ) Notice: Subject to any disclaimer, the term of this patent is extended or adjusted under 35 U.S.C. 154(b) by 284 days.

(21) Appl. No.: 15/255,357

(22) Filed: Sep. 2, 2016

(65) Prior Publication Data
US 2016/0366971 A1 Dec. 22, 2016

Related U.S. Application Data

(62) Division of application No. 13/527,107, filed on Jun. 19, 2012, now Pat. No. 9,486,363.

(51) Int. Cl.
A42B 3/22 (2006.01)
A61F 9/06 (2006.01)
A42C 2/00 (2006.01)

(52) U.S. Cl.
CPC .............. A61F 9/061 (2013.01); A42B 3/225 (2013.01); A42C 2/00 (2013.01); A61F 9/06 (2013.01); Y10T 29/49826 (2015.01)

(58) Field of Classification Search
CPC ... A61F 9/061; A61F 9/06; A42C 2/00; Y10T 29/49826; A42B 3/225
See application file for complete search history.

(56) References Cited

U.S. PATENT DOCUMENTS

| 1,378,255 | A | 5/1921 | Malcolm |
| 1,800,623 | A | 4/1931 | Green |
| 2,171,052 | A | 8/1939 | Tatter |
| 2,190,074 | A | 2/1940 | Locher |
| 2,354,502 | A | 7/1944 | Cockrill et al. |
| 2,420,619 | A | 5/1947 | Rakos |
| 2,686,309 | A | 8/1954 | Burdick |
| 2,896,215 | A | 7/1959 | Fernandez |

(Continued)

FOREIGN PATENT DOCUMENTS

| DE | 537469 | 11/1931 |
| WO | WO2013044787 | 4/2013 |

Primary Examiner — Richale L Quinn
(74) Attorney, Agent, or Firm — McClure, Qualey & Rodack, LLP

(57) ABSTRACT

A protective helmet having a cover plate over a front vision area and a cover plate knock out assembly for moving the cover plate a predetermined distance away from the helmet so that a finger of a user can get behind the cover plate to enable its removal from the front vision area of the helmet. The cover plate knock out assembly comprises a step-shaped actuator element and a light blocking cover. The upper portion of the step-shaped actuator pushes the cover plate away from the helmet when the lower portion of the step-shaped actuator is pressed. The cover plate made of clear plastic includes a spring tendency when slightly compressed when attached to the helmet thereby pushing the upper portion of the step-shaped actuator into a resting position in the helmet.

5 Claims, 9 Drawing Sheets

(56) References Cited

U.S. PATENT DOCUMENTS

| | | | | |
|---|---|---|---|---|
| 3,086,213 A * | 4/1963 | Crozat | | A61F 9/061 2/8.3 |
| 3,490,071 A * | 1/1970 | Marshall | | A61F 9/061 2/8.3 |
| 3,768,099 A * | 10/1973 | Manz | | A61F 9/061 2/8.3 |
| 4,524,465 A | 6/1985 | Huber | | |
| 4,539,713 A | 9/1985 | Hodge | | |
| 4,694,507 A * | 9/1987 | Owen | | A61F 9/061 2/8.3 |
| 4,860,389 A * | 8/1989 | Morin | | A42B 3/223 2/424 |
| 5,084,918 A | 2/1992 | Breining et al. | | |
| 5,224,219 A * | 7/1993 | Edwards | | A61F 9/061 2/8.3 |
| 5,398,341 A * | 3/1995 | Trapple | | A61F 9/061 2/8.3 |
| 5,553,329 A * | 9/1996 | Casartelli | | A42B 3/223 2/424 |
| 5,561,855 A | 10/1996 | McFall | | |
| 6,185,739 B1 | 2/2001 | Verkic et al. | | |
| 6,507,984 B2 | 1/2003 | Sanchez | | |
| 7,308,719 B2 | 12/2007 | Huh | | |
| D565,801 S | 4/2008 | Curci et al. | | |
| 8,745,763 B2 * | 6/2014 | Cho | | A42B 3/223 2/15 |
| 8,776,263 B1 * | 7/2014 | Fitos | | A61F 9/062 2/8.3 |
| 9,861,530 B2 * | 1/2018 | Lilenthal | | A61F 9/065 |
| 2005/0273900 A1 | 12/2005 | DeYoung | | |
| 2006/0185052 A1 * | 8/2006 | Huh | | A61F 9/06 2/8.2 |
| 2007/0089216 A1 * | 4/2007 | Walkden | | A61F 9/061 2/8.7 |
| 2013/0333089 A1 * | 12/2013 | Watkins | | A61F 9/06 2/8.3 |

* cited by examiner

PROTECTIVE HELMET HAVING A COVER PLATE KNOCK OUT ASSEMBLY

This application is a Divisional Application of prior application Ser. No. 13/537,107, filed Jun. 19, 2012, now allowed

IN THE SUMMARY OF THE INVENTION

Background of the Invention

Field of the Invention

The present invention relates generally to a protective helmet and more particularly to a cover plate knock out assembly to facilitate removal of the cover plate from the helmet without the cover plate popping out.

Description of Related Art

The cover plates in the prior art have been mechanically secured with gaskets around front cover plate and in front of a light filter. Examples of the prior art patent documents are as follows:

U.S. Pat. No. 2,354,502 issued Jul. 25, 1944 to W. T. Cockrilf et al. discloses a heat shield for use in arc welding, grinding, painting, etc. having a latch on a lower portion of the hood front for securing an outer shield in closed or operation position on the inner shield. However, this design requires a hinge and a latch for operating the outer shield. Operational components such as a light filter are not moved in the present invention.

U.S. Pat. No. 4,860,389 discloses a protective helmet with a movable transparent screen having a slide associated with a push button which bears on an inner face of the screen for releasing the screen from closure on the helmet a sufficient amount to allow a finger to be placed between the helmet and the screen so as to manually raise the screen and open the aperture of the helmet. However, this design relies on a pivot point via a shaft and spring properties of the slide to return the slide to its resting position. Therefore, additional parts are required.

U.S. Pat. No. 5,084,918 issued Feb. 4, 1992 to Peter M. Breining et al. discloses a safety helmet having a chin guard which locks in a closed position and comprises an opening bar for releasing the chin guard so it may swivel upward by means of hinges. However, this design requires additional parts not needed in the present invention.

SUMMARY OF THE INVENTION

Accordingly, it is therefore an object of this invention to provide a protective helmet having a cover plate knock out assembly for easily starting removal of the cover plate.

It is an object of this invention to provide an upper portion of a step-shaped actuator of the cover plate knock out assembly adjacent to a lower portion of the cover plate to move said cover plate a predetermined distance away from the helmet to enable fingers of a user to pull the cover plate out of the helmet.

It is yet another object of this invention to move said cover plate the predetermined distance away from the helmet whereby the cover plate will not pop out of the helmet and will not create a potential hazard due to the motion of the ejected cover plate which has sharp corners.

It is a further object of this invention to prevent any fumes or light from entering the helmet in the vision area by the knock out cover plate in the knock out assembly.

These and other objects are further accomplished by a protective helmet comprising a shell forming a helmet having a front vision area, a see-through cover plate removably secured to the front vision area of the helmet, a knock out assembly having an upper portion of a step-shaped actuator positioned adjacent to a lower portion of the cover plate, and the lower portion of the step-shaped actuator extending from a rear portion of the knock out assembly. The helmet includes a welding protective helmet. The cover plate slides into channels or guides on opposite sides of the helmet. A lower edge of the cover plate is moved away from the helmet a predetermined distance by the upper portion of the step-shaped actuator when the lower portion of the step-shaped actuator is pressed toward the cover plate, the predetermined distance prevents the cover plate from popping out of the helmet. The cover plate when secured to the protective helmet comprises a tendency to return to a normal flat state thereby pushing the upper portion of the step-shaped actuator into its resting position. The knock out assembly comprises a light blocking cover enclosing the step-shaped actuator of the knock out assembly to block any light from entering an interior of the helmet when the lower portion is in its resting position. The upper portion of the step-shaped actuator extends from a front opening in a lower polyland of the shell of the helmet adjacent to the lower portion of the cover plate.

The objects are further accomplished by a cover plate knock out assembly for attaching to a protective helmet comprising a step-shaped actuator, a light blocking cover for securing the step-shaped actuator in the protective helmet wherein an end of the upper portion of the step-shaped actuator rests adjacent to a lower portion of a cover plate of the helmet, a land extending from a wall of the light blocking cover for supporting the step-shaped actuator, a U-shaped upper snap lock protruding from an upper portion of the wall of the light blocking cover for securing the upper portion of the light blocking cover to the protective helmet, and a wedge shaped lower snap lock protruding upward from a bottom wall of the light blocking cover for securing the lower portion of the light blocking cover to the protective helmet. The upper portion of the step shaped actuator extends upward from an end of the lower portion forming a right angle and extending away from the lower portion a predetermined distance. The light blocking cover plate comprises an opening for the lower portion of the step-shaped actuator to extend through.

The objects are further accomplished by providing a method of making a protective helmet comprising the steps of forming a shell of a helmet having a front vision area, securing a see through removable cover plate to the front vision area of the helmet, positioning a knock out assembly having an upper portion of a step-shaped actuator positioned adjacent to a lower portion of the cover plate, and extending the lower portion of the step-shaped actuator through an opening in a rear portion of the knock out assembly.

Additional objects, features and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENT

Figure 1:
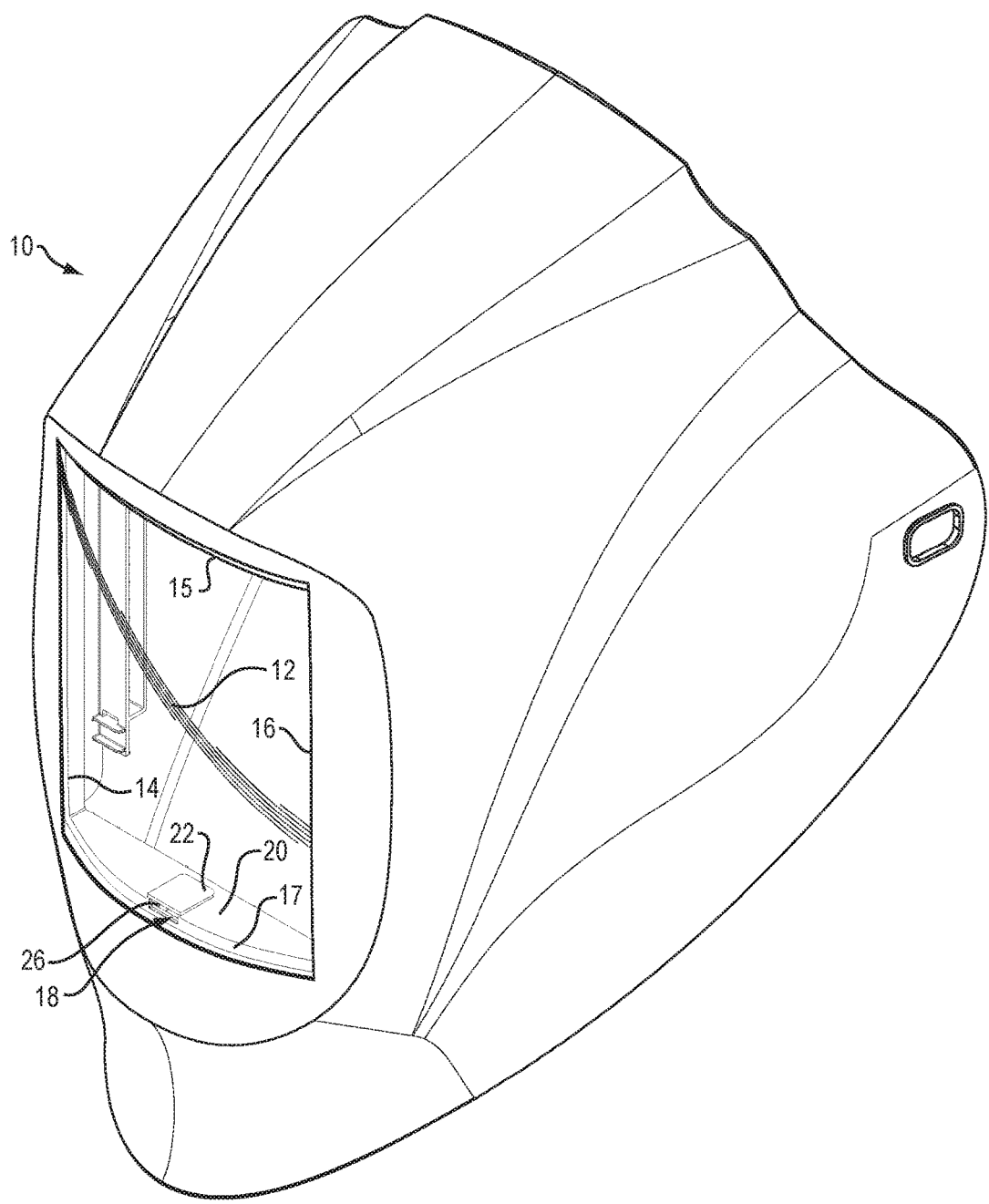
FIG. 1 is a front perspective view of a protective helmet having a cover plate and a cover plate knock out assembly according to the present invention.
Figure 2:
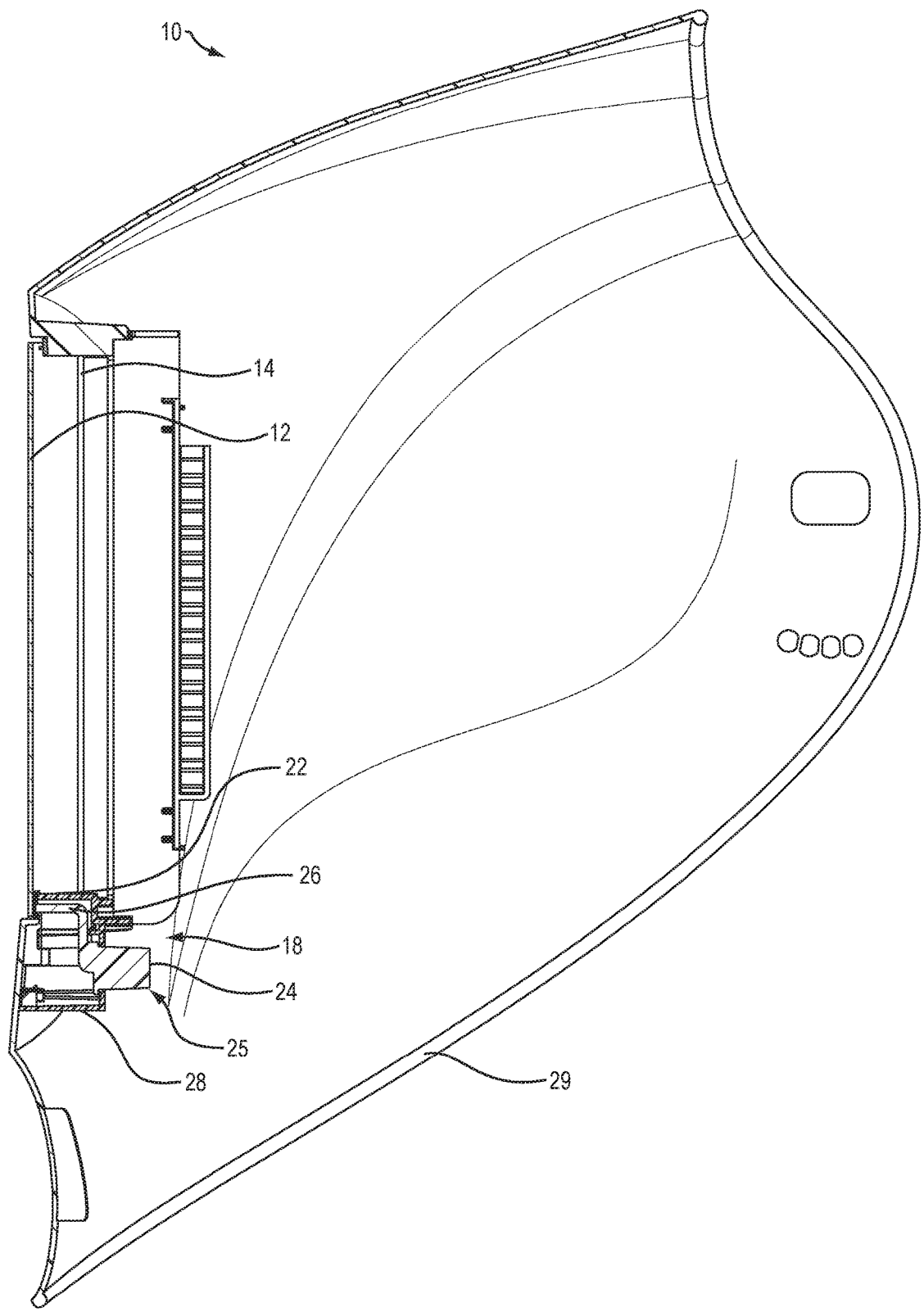
FIG. 2 is a cross-section of the protective helmet of FIG. 1 showing the cover plate knock out assembly having an upper portion of a step-shaped actuator adjacent to the lower portion of the cover plate.

Referring to FIG. 1 and FIG. 2, FIG. 1 is a front perspective view of a protective helmet 10 such as a welding protective helmet having a cover plate 12 and a cover plate knock out assembly 18 according to the present invention. The see through cover plate 12 fits into channels 14, 16 on opposite sides of a front vision area of the protective helmet 10 and the upper and lower edges of the cover plate 12 rest against polylands 15, 17 surfaces designed into the upper and lower vision perimeter areas of the helmet. FIG. 2 is a cross-section of protective helmet 10 of FIG. 1 showing the knock out assembly 18 comprising a step-shaped actuator 25 and a light blocking cover or assembly cover 28. The step-shaped actuator 25 includes an upper portion 26 positioned adjacent to a lower portion of the cover plate 12 and a lower portion 24 that extends though the rear of the light blocking cover 28 to outside of the light blocking cover assembly 28.

The cover plate 12 protects a light filter normally mounted in a welding protective helmet 10 from any spatter during a welding process, and because of the tight fit of the cover plate 12 around the edges of the vision area of the protective helmet 10, welding fumes and spatter are prevented from entering the interior of the protective helmet 10.

Figure 3:
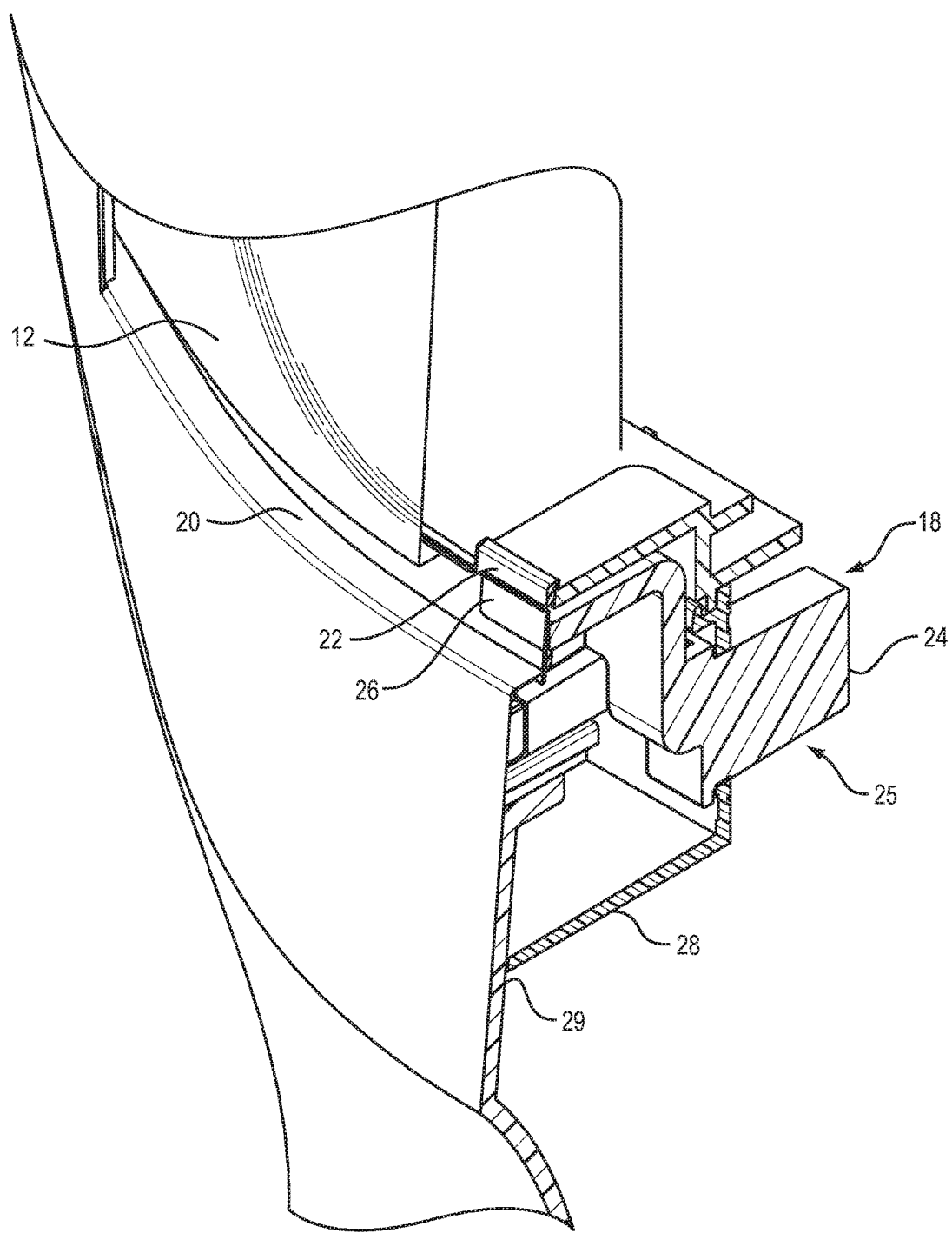
FIG. 3 is an enlarged perspective cross-section of the step-shaped actuator mounted in the cover plate knock out assembly.

Referring to FIG. 2 and FIG. 3, FIG. 3 shows an enlarged perspective cross-section view of the step-shaped actuator 25 mounted in the cover plate knock out assembly 18. An opening is provided in a raised area 22 of a lower polyland 20 of the welding protective helmet 10 for the upper portion 26 to extend through to be adjacent to the cover plate 12. The lower portion 24 the step-shaped actuator 25 extends out of the light blocking cover 28 away from the cover plate 12. The center raised area 22 of the lower polyland 20 of the welding protective helmet 10 is raised to accommodate the positioning of the upper portion 26 of the step-shaped actuator 25 so that it contacts the lower portion of the cover plate 12 just above a bottom edge of the cover plate 12.

Figure 4:
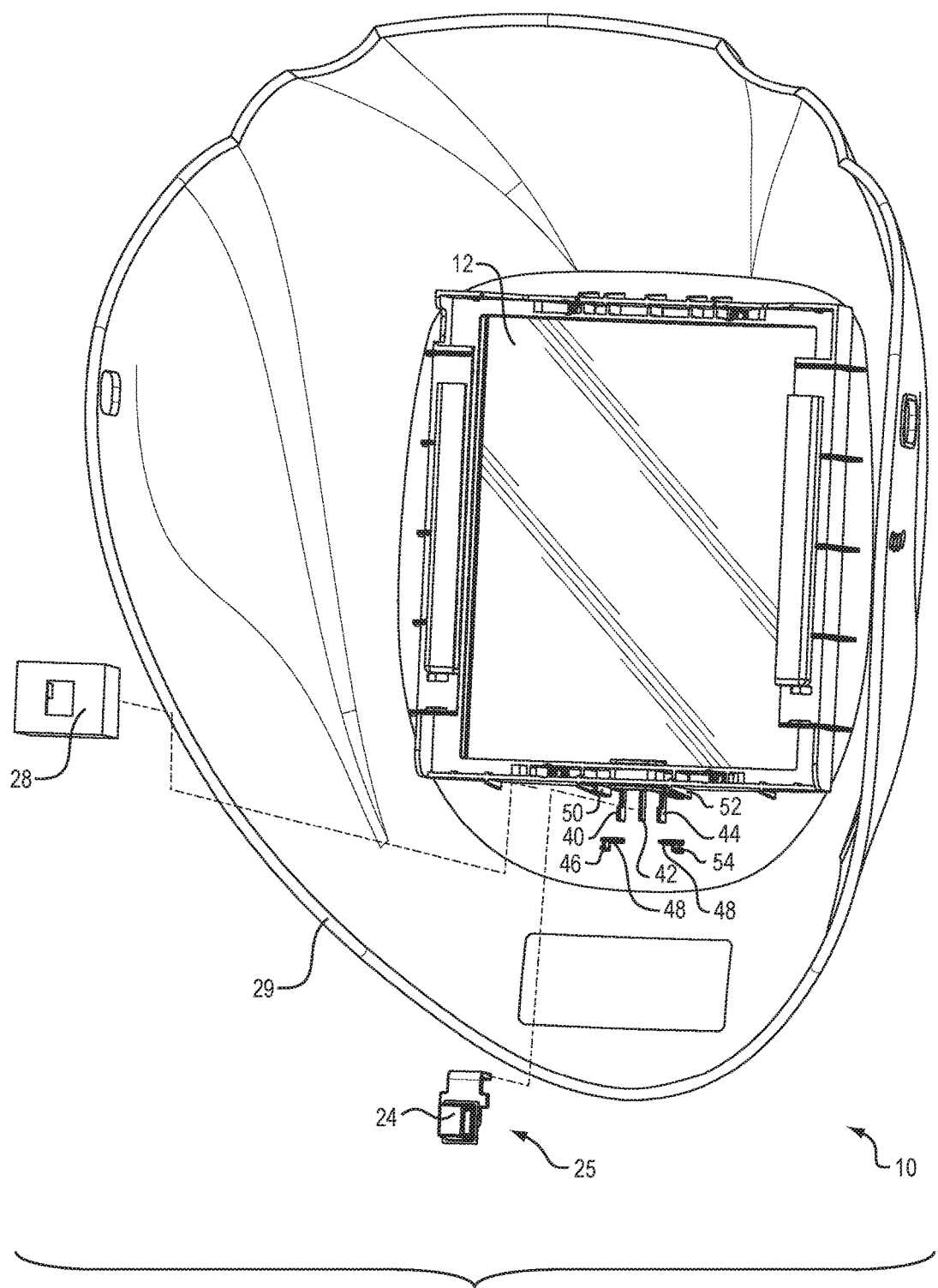
FIG. 4 is an exploded rear perspective view of the cover plate knock out assembly which attaches on the inside of the protective helmet immediately under the cover plate.

Referring to FIG. 4, an expanded rear view of the cover plate knock out assembly 18 shows the lower portion 24 of the step-shaped actuator 25 and the light blocking cover 28 which attaches to the guides 40-52 on the shell 29 of protective helmet 10 immediately under that cover plate 12.

The step-shaped actuator 25 is made of rigid plastic (ABS). The light blocking cover 28 is made of semi-rigid plastic for performing a proper snap (32) function (Nylon). The protective helmet 10 is made of durable high heat/low cold performing plastic (Nylon). The cover plate 12 is made of clear, impact resistant plastic (PC).

Figure 5:
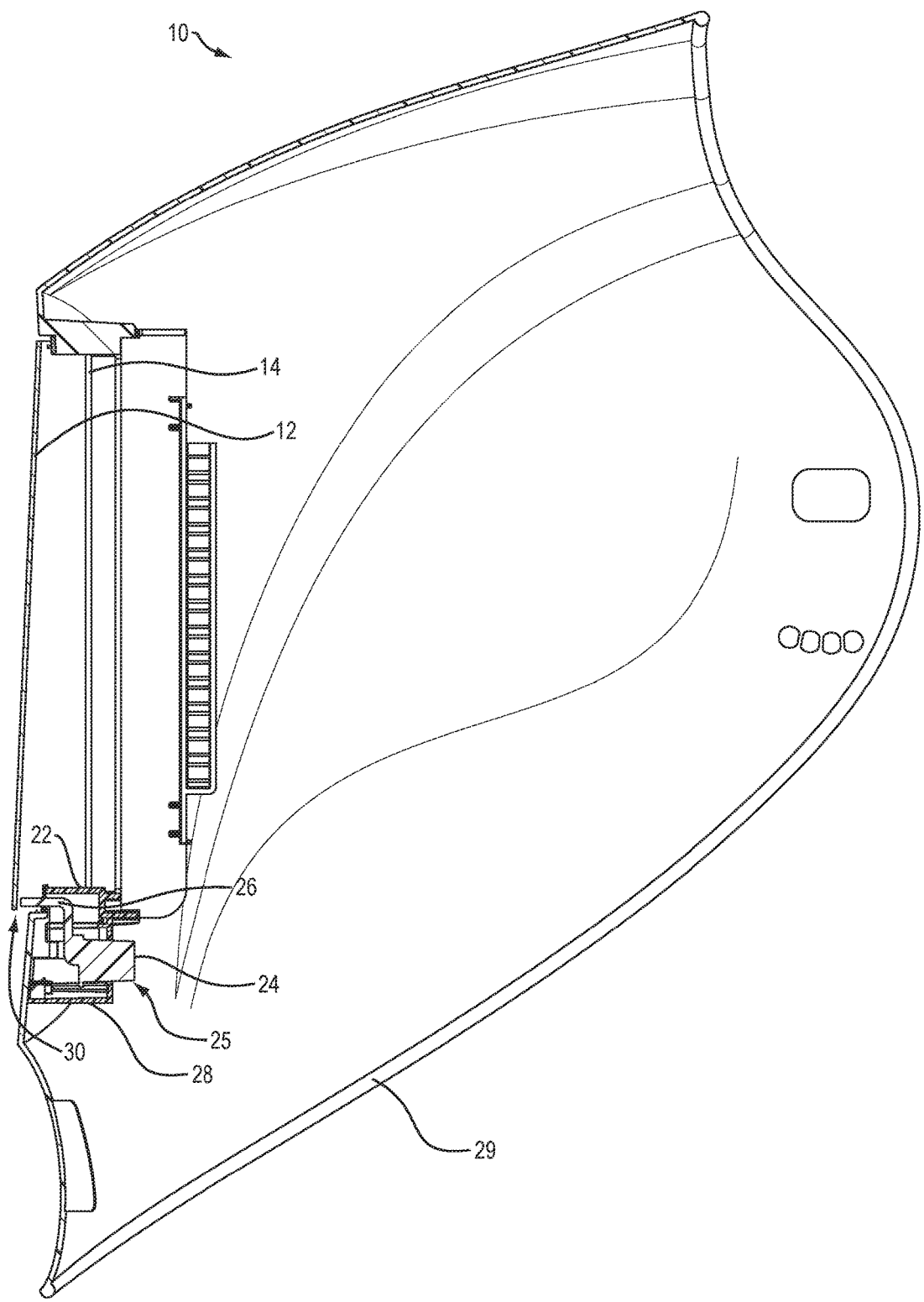
FIG. 5 is a cross-section of the protective helmet with the lower portion of the cover plate pushed out a predetermined distance by the knock out upper portion of the step-shaped actuator.

Referring to FIG. 5, a cross-section of the protective helmet 10 is shown with the lower portion of the cover plate 12 being pushed outwardly away 30 from the raised polyland 22 and protective helmet 10 because the lower portion 24 of the step-shaped actuator 25 is pressed moving the upper portion 26 through the hole in the raised polyland. When the upper portion 26 is fully extended a predetermined distance, a user's finger can get under the bottom of the cover plate 12 and easily pull it from the protective helmet 10. The predetermined distance is determined by the length of the upper portion 26 of the step-shaped actuator 25, and it is limited to a length whereby when the upper portion 26 is fully extended, the cover plate 12 will not pop out of the protective helmet 10. In the present embodiment, the upper portion 26 extends approximately 0.375 inches beyond the raised areas 22 of the lower polyland 20.

Figure 6:
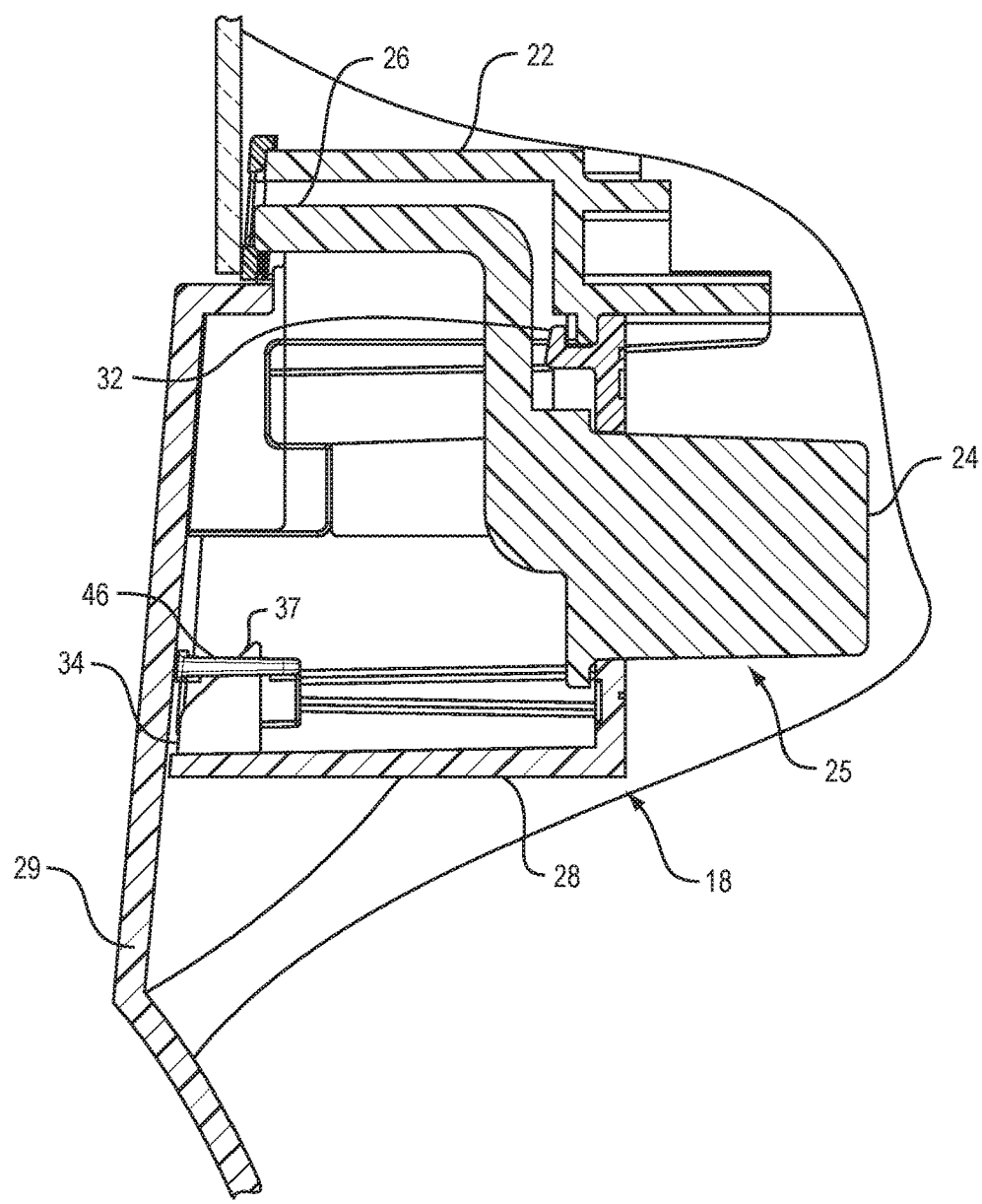
FIG. 6 is an enlarged cross-section of the cover plate knock out assembly showing an upper snap lock and a lower snap lock of a light blocking cover for securing the light blocking cover to a shell of the protective helmet.

Referring to FIG. 6, an enlarged cross-section of the cover plate knock out assembly 18 shows a U-shaped upper snap lock 32 and a partial wedge shaped lower snap lock 34 extending upward from a bottom wall of the light blocking cover 28 both of which firmly secure the step-shaped actuator 25 and light blocking cover 28 to the shell 29 of the protective helmet 10. The wedge portion 37 of the lower snap lock 34 faces the shell 29 of the protective helmet 10 so that the wedge portion 37 slides into snap catch loop 46 extending from the inside of shell 29.

Figure 7:
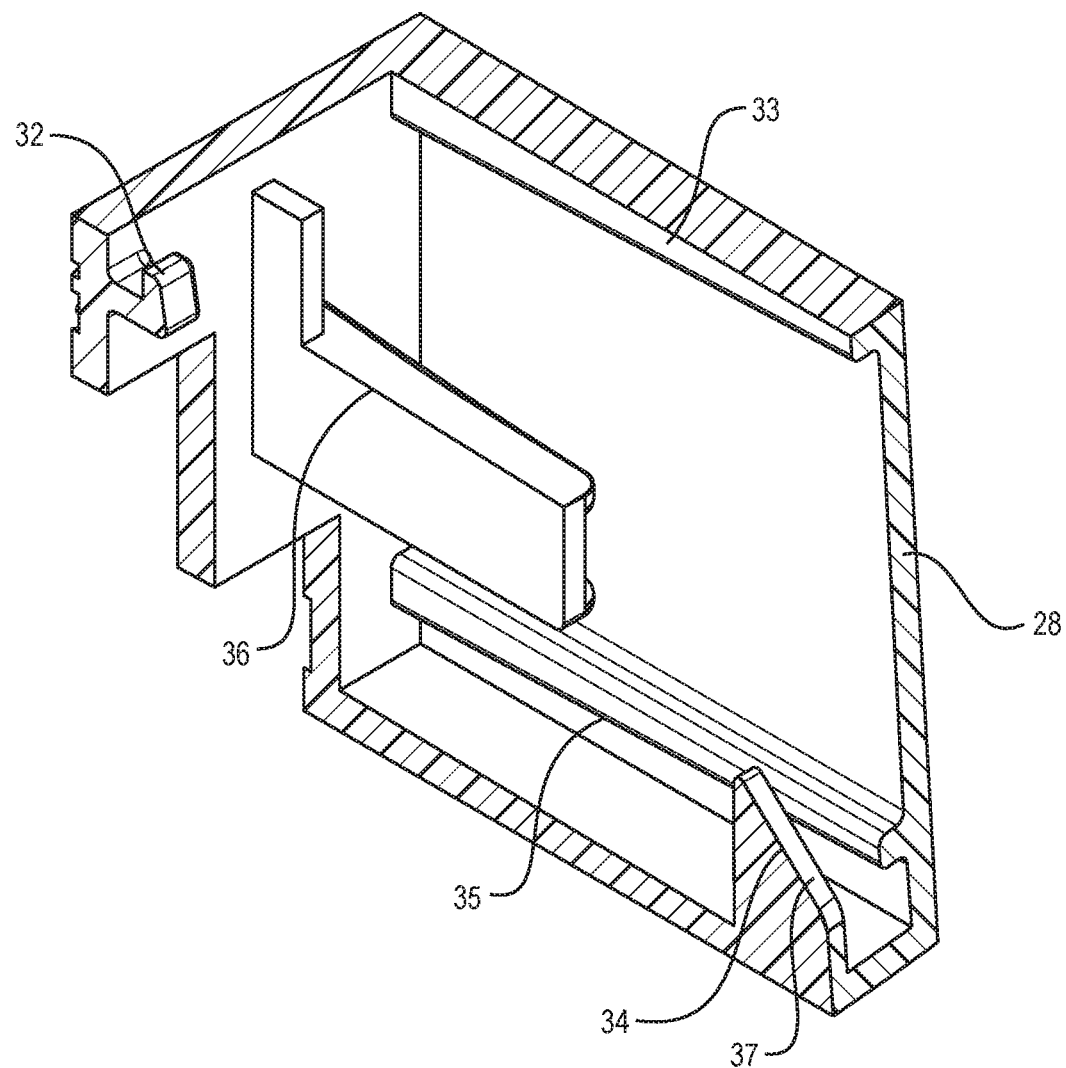
FIG. 7 is a partial cross-section perspective inside view of the light blocking cover showing a land for supporting the upper portion of the step-shaped actuator, an upper snap lock, a lower snap lock, an upper guide rail and a lower guide rail for aligning and guiding the light block cover into the welding helmet, and a land rail for supporting the movement of the step-shaped actuator of the cover plate knock out assembly.

Referring to FIG. 7, a partial cross-section perspective inside view of the light blocking cover 28 shows a land 36 for supporting the step-shaped actuator 25. Also shown are the U-shaped upper snap lock 32 and lower snap lock 34 having the wedge portion 37 both of which are used for securing the light blocking cover 28 to the shell 29 of the protective helmet 10. In addition, upper guide rail 33 and lower guide rail 35 provide guidance when attaching and aligning the light blocking cover 28 to the shell 29 of the protective helmet 10. A land rail 36 supports the movement of the step-shaped actuator 25 of the cover plate knock out assembly 18.

Figure 8A:
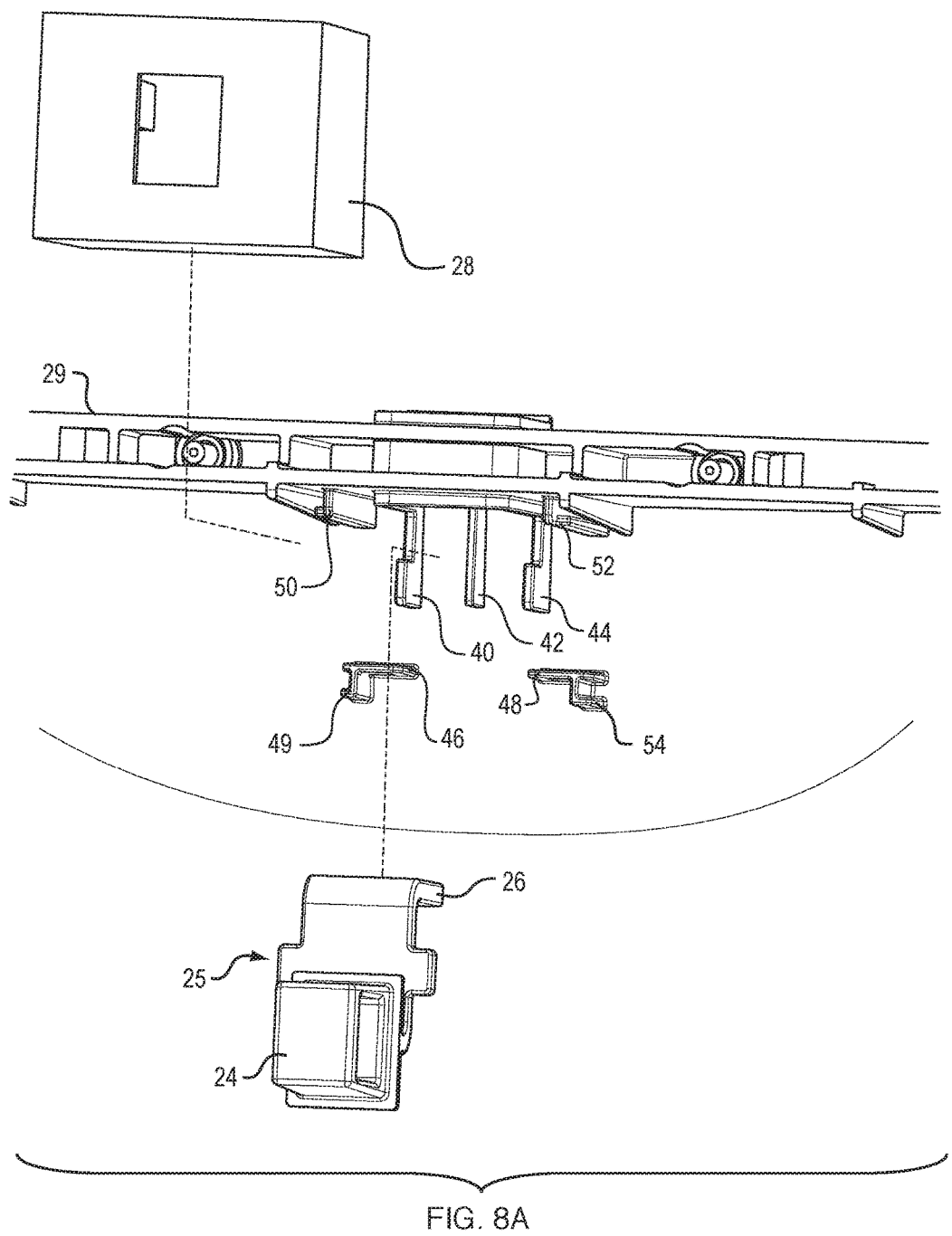
FIG. 8A is an enlarged perspective view from inside the helmet showing knock out cover plate assembly guides, lower snap mating elements and snap catch loops on an inside lower portion of the helmet shell where the light blocking cover attaches to the helmet shell.
Figure 8B:
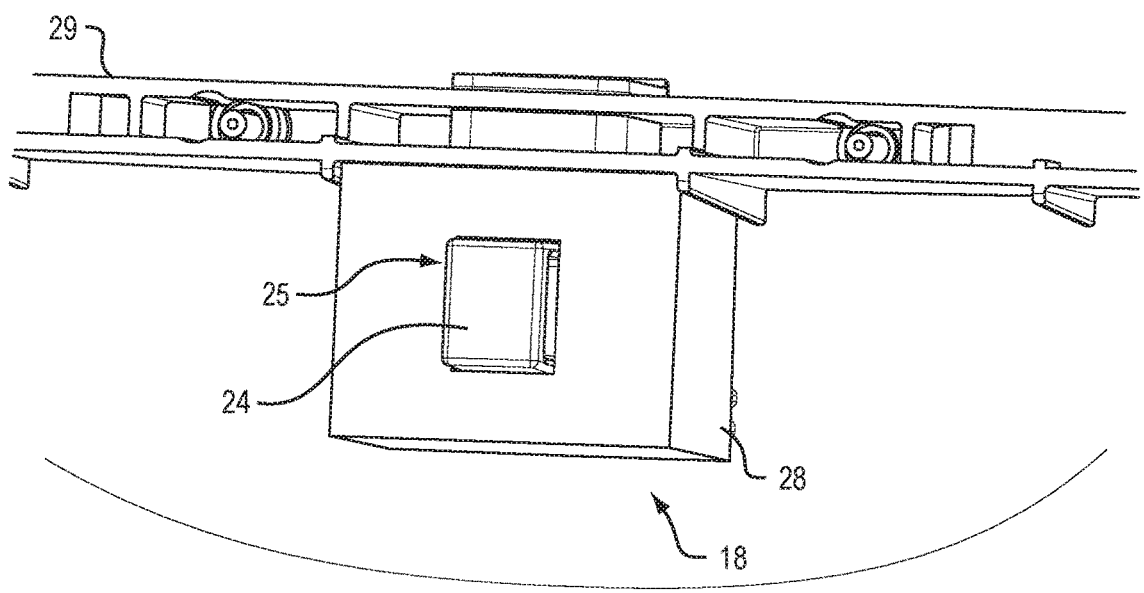
FIG. 8B is a perspective view of the cover plate knock out assembly attached to the inside of the protective helmet under the cover plate.

Referring to FIGS. 8A and 8B, FIG. 8A shows an enlarged perspective view of the area under the cover plate 12 inside the protective helmet 10 where the light blocking cover 28 attaches along with the step-shaped actuator 25 to the protective helmet 10. Knock out assembly guides 40, 44, 50, and 52 are provided for guiding the upper guide rail 33 and land rail 36 of cover 28 when attached to the shell 29 of the protective helmet 10. A stop 42 is provided between assembly guides 40, 44 to prevent the slide from rotating too much when installing during production. Also, snap catch loops 46, 48 are provided for receiving the wedge shaped lower snap locks 34 in the light blocking cover 28 where the lower guide rail 35 of cover 28 slides into lower guides 49 and 54 of protective helmet shell 29. FIG. 8B is a perspective view showing the cover plate knock out assembly 18 securely attached to the inside of the protective helmet 10 under the cover plate 12.

This invention has been disclosed in terms of a preferred embodiment. It will be apparent that many modifications can be made to the disclosed apparatus and method without departing from the invention. Therefore, it is the intent of the appended claims to cover all such variations and modifications as come within the true spirit and scope of this invention.

What is claimed is:

1. A method of making a protective helmet comprising the steps of forming a shell of a helmet having a front vision area;

securing a see-through removable cover plate to said front vision area of said helmet;

positioning a knock out assembly having an upper portion of a step-shaped actuator positioned adjacent to a lower portion of said cover plate; and extending said lower portion of said step-shaped actuator through an opening in a rear portion of said knock out assembly;

wherein said step of positioning said knock out assembly comprises the step of providing a light blocking cover enclosing said step-shaped actuator of said knock out assembly to block any light from entering an interior of said helmet when the lower portion is in its resting position.

2. The method as recited in claim 1 wherein said protective helmet is a welding helmet.

3. The method as recited in claim 1 wherein said step of securing said removable cover plate comprises the step of sliding said cover plate into channels on opposite sides of said protective helmet.

4. The method as recited in claim 1 wherein said step of positioning said knock out assembly adjacent to a lower portion of said cover plate comprises the step of moving a lower edge of said cover plate away from said helmet a predetermined distance by said upper portion of said step-shaped actuator when said lower portion of said step-shaped actuator is pressed, said predetermined distance preventing said cover plate from popping out of said helmet.

5. The method as recited in claim 4 wherein said method comprises the step of providing said cover plate with a tendency to return said cover plate to a normal flat state thereby pushing said upper portion of said step-shaped actuator into its resting position.

* * * * *